United States Patent
Gallenkamp et al.

(10) Patent No.: US 10,384,995 B2
(45) Date of Patent: Aug. 20, 2019

(54) METHOD FOR PREPARING SUBSTITUTED STYRENE DERIVATIVES

(71) Applicant: Bayer CropScience Aktiengesellschaft, Monheim am Rhein (DE)

(72) Inventors: Daniel Gallenkamp, Wuppertal (DE); Mark James Ford, Wiesbaden-Breckenhelm (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 16/324,159

(22) PCT Filed: Aug. 7, 2017

(86) PCT No.: PCT/EP2017/069926
§ 371 (c)(1),
(2) Date: Feb. 8, 2019

(87) PCT Pub. No.: WO2018/029140
PCT Pub. Date: Feb. 15, 2018

(65) Prior Publication Data
US 2019/0177256 A1 Jun. 13, 2019

(30) Foreign Application Priority Data
Aug. 12, 2016 (EP) .................. 16183948

(51) Int. Cl.
| | | |
|---|---|---|
| *A01N 31/08* | (2006.01) | |
| *C07C 33/28* | (2006.01) | |
| *C07C 37/00* | (2006.01) | |
| *C07C 37/06* | (2006.01) | |
| *C07C 309/66* | (2006.01) | |
| *C07C 309/73* | (2006.01) | |
| *C07C 39/373* | (2006.01) | |

(52) U.S. Cl.
CPC .......... *C07C 37/002* (2013.01); *A01N 31/08* (2013.01); *C07C 33/28* (2013.01); *C07C 37/06* (2013.01); *C07C 39/373* (2013.01); *C07C 309/66* (2013.01); *C07C 309/73* (2013.01)

(58) Field of Classification Search
CPC ..... C07C 37/002; C07C 37/06; C07C 303/28; C07C 309/73; C07C 309/66; C07C 39/373; A01N 31/08
See application file for complete search history.

(56) References Cited

U.S. PATENT DOCUMENTS

| | | |
|---|---|---|
| 5,424,460 A | 6/1995 | Duhamel et al. |
| 8,759,527 B2 | 6/2014 | Tsuchiya et al. |
| 9,006,266 B2 | 4/2015 | Tsuchiya et al. |
| 9,150,565 B2 | 10/2015 | Tsuchiya et al. |
| 9,434,723 B2 | 9/2016 | Tsuchiya et al. |
| 9,770,027 B2 | 9/2017 | Tsuchiya et al. |
| 9,930,890 B2 | 4/2018 | Tsuchiya et al. |
| 10,160,707 B2 | 12/2018 | Erver et al. |
| 2012/0122929 A1 | 5/2012 | Tsuchiya et al. |
| 2013/0296272 A1 | 11/2013 | Tsuchiya et al. |
| 2014/0206646 A1 | 7/2014 | Tsuchiya et al. |
| 2015/0175598 A1 | 6/2015 | Tsuchiya et al. |
| 2015/0351403 A1 | 12/2015 | Tsuchiya et al. |
| 2016/0309719 A1 | 10/2016 | Tsuchiya et al. |
| 2018/0007903 A1 | 1/2018 | Tsuchiya et al. |

FOREIGN PATENT DOCUMENTS

| | | |
|---|---|---|
| WO | 2012025557 A1 | 3/2012 |
| WO | 2015189114 A1 | 12/2015 |

OTHER PUBLICATIONS

International Search Report issued in counterpart Application No. PCT/EP2017/069926, dated Oct. 17, 2017.
F. Dubnikova et al, "Isomerisation of dihydrobenzofuran and isodihydrobenzofuran. Quantum chemical and kinetics calculations"; J. Phys. Chem. A; (2002), vol. 106: 9278-9283.
Karakhanov et al., "Synthesis of 2-hydroxystrene derivatives" Academician O. A. Reutov. (1978) vol. 239, No. 6 p. 1357, Engl. Translation.
Huisgen et al., "Nucleophile aromatische Substitutionen" Aus Dem Institut Fur Organische Chemie Der Universitaet Muenchen. (1960) 1496-1506.

*Primary Examiner* — Jafar F Parsa
(74) *Attorney, Agent, or Firm* — McBee Moore Woodward & Vanik IP, LLC

(57) ABSTRACT

The present invention relates to a method for preparing substituted styrene derivatives.

6 Claims, No Drawings

METHOD FOR PREPARING SUBSTITUTED STYRENE DERIVATIVES

CROSS-REFERENCE TO RELATED APPLICATIONS

This application is a National Stage entry of International Application No. PCT/EP2017/069926, filed Aug. 7, 2017, which claims priority to European Patent Application No. 16183948.5, filed Aug. 12, 2016.

BACKGROUND

Field

The present invention relates to a method for preparing substituted styrene derivatives.

Description of Related Art

It is already known that substituted styrene derivatives are useful intermediates in the preparation of active agrochemical ingredients (see WO 2012/025557 for example).

Various methods for preparing such substituted styrene derivatives are described in the literature.

A possible method for preparing 3-chloro-2-vinylphenol is described in WO 2015/189114 and U.S. Pat. No. 5,424,460. The preparation is effected by aromatization of 2,2,6-trichloro-1-vinyl-7-oxabicyclo[4.1.0]heptane under basic conditions. A disadvantage of this method is the use of an organometallic reagent for preparing 2,2,6-trichloro-1-vinyl-7-oxabicyclo[4.1.0]heptane and also the tendency of this precursor to oligomer or polymer formation during the preparation.

An alternative and general possibility for preparing 2-vinylphenols consists of the ring-opening of 2,3-dihydrobenzofurans under basic conditions. For example, the treatment of 2,3-dihydrobenzofuran with 2.3 equivalents of $LiNH_2$ as base in HMPA or DMSO at a temperature of 20 to 60° C. and a reaction time of five hours affords 2-vinylphenol with a yield of 95% (*Doklady Akademil Nauk SSSR* 1978, 239, 1357). A disadvantage of this method is the use of $LiNH_2$ as very strong base and HMPA or DMSO as solvent since these substances are unsuitable for industrial use. The treatment of 2,3-dihydrobenzofuran with 1.5 equivalents of $LiNEt_2$ as base in diethyl ether at a temperature of 35° C. and a reaction time of forty-five hours affords 2-vinylphenol with a yield of 25% (*Chem. Ber.* 1960, 93, 1496). A disadvantage of this method is the use of $LiNEt_2$ as very strong base and diethyl ether as solvent since these substances are unsuitable for industrial use. Moreover, a low yield of 25% of 2-vinylphenol is achieved by the method described and a very long reaction time is required. For these reasons, the method is unsuitable for industrial use.

Due to the importance of substituted styrene derivatives as a unit for synthesis of novel active agrochemical ingredients, the problem addressed is that of finding a method which can be used on an industrial scale and inexpensively and which circumvents the disadvantages described above. It is also desirable to obtain the specific styrene derivatives with high yield and high purity, such that the target compound preferably does not have to be subjected to any further potentially complex purification.

SUMMARY

This object is achieved by a method for preparing substituted styrene derivatives of the formula (I):

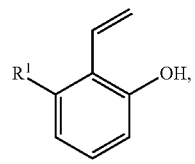

where
$R^1$ is Cl (Ia), Br (Ib) or methyl (Ic),
characterized in that a dihydrobenzofuran derivative of the formula (II)

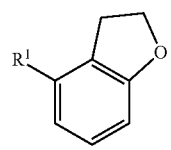

where
$R^1$ is Cl, Br or methyl
is reacted by heating in the presence of an alkoxide or hydroxide base
to give compounds of the formula (I).

DETAILED DESCRIPTION OF A PREFERRED EMBODIMENT

Preference is given to a method according to the invention in which the radical definitions of the formulae (I) and (II) are as follows:
$R^1$ is Cl.

Description of the Process

The reaction according to the invention is shown in Scheme 1.

Scheme 1

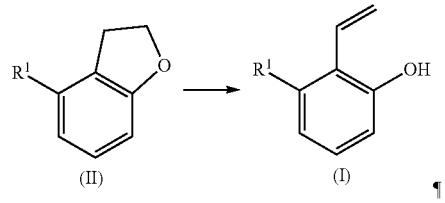

The desired styrene derivatives of the general formula (I) are obtained with good yields and in high purity by the method according to the invention.

The method according to the invention has the advantage over the methods described above that the starting materials can be prepared on the industrial scale and, surprisingly, the method can be carried out successfully by using weaker bases such as potassium hydroxide.

Useful solvents for the method according to the invention in principle include any organic solvents or solvent mixtures that are inert under the reaction conditions, including: ethers (such as: 1,2-dimethoxyethane (DME), diglyme, tetrahydrofuran (THF), 2-methyl-THF, anisole and 1,4-dioxane);

amide solvents (such as: DMF, N,N-dimethylacetamide (DMAc)) and dipolar aprotic solvents (such as: DMSO). Preference is given to using THF, 2-methyl-THF, dioxane, DME, anisole, diglyme, DMF or DMAc or mixtures of DMAc with ethers or mixtures of DMAc with aromatic solvents (such as: toluene, xylene, chlorobenzene or 1,2-dichlorobenzene). Particular preference is given to using DMAc, DMF or diglyme or mixtures of DMAc or DMF with THF, 2-methyl-THF, dioxane, DME, toluene, xylene, chlorobenzene or 1,2-dichlorobenzene.

Examples of useful alkoxide bases for the method according to the invention include the following: potassium tert-butoxide, sodium tert-butoxide, sodium methoxide, sodium ethoxide or potassium methoxide. Examples of useful hydroxide bases for the method according to the invention include the following: potassium hydroxide. Preference is given to using potassium hydroxide, potassium tert-butoxide, sodium tert-butoxide or sodium methoxide. Particular preference is given to using potassium hydroxide or potassium tert-butoxide.

Particularly preferred are the following combinations of the groups of solvents and bases described above:
a) diglyme in combination with potassium hydroxide
b) DMAc in combination with potassium hydroxide
c) DMF in combination with potassium hydroxide
d) solvent mixture of DMAc with toluene, xylene, chlorobenzene, 1,2-dichlorobenzene, dioxane, DME, 2-methyl-THF or THF in combination with potassium hydroxide
e) solvent mixture of DMF with toluene, xylene, chlorobenzene, 1,2-dichlorobenzene, dioxane, DME, 2-methyl-THF or THF in combination with potassium hydroxide
f) DMAc, DMF, THF, 2-methyl-THF, dioxane, DME, anisole or diglyme or mixtures of these solvents in combination with potassium tert-butoxide.

Especially preferred for the method according to the invention is the following combination of solvents and base: DMAc or diglyme and potassium hydroxide.

The temperature in the method according to the invention can be varied within wide limits. A customary operating temperature is from 20° C. to 120° C. The reaction is preferably conducted at a temperature in the range of 80° C. to 120° C. The reaction is particularly preferably conducted at a temperature in the range of 100° C. to 120° C.

The method according to the invention is typically conducted at standard pressure. It is also possible to conduct the reaction under reduced pressure or at elevated pressure (positive pressure).

The molar ratios of the compound of the formula (II) to bases of the group described above may be varied within wide limits. Typically, a molar ratio from 1:1 to 1:5 is employed. For organic bases such as potassium tert-butoxide, a molar ratio from 1:1 to 1:1.5 is preferred. Particular preference is given to a molar ratio of 1:1.1. For inorganic bases such as potassium hydroxide, a molar ratio from 1:2 to 1:4 is preferred. Particular preference is given to a molar ratio of 1:3.

The reaction time is short and is in the range from about 0.5 to about 5 hours. A longer reaction time is possible, but is not economically worthwhile.

The compounds of the formula (I) are not isolated. The compounds of the formula (I) are further reacted to compounds of the formula (III) (Scheme 2), either directly (when using potassium tert-butoxide as base) or after an intermediate work-up (when using potassium hydroxide as base).

The reaction to give compounds of the formula (III) is carried out as described in WO 2015/189114.

The following reaction sequence is preferably carried out for preparing the compound of the formula (III):

Scheme 2

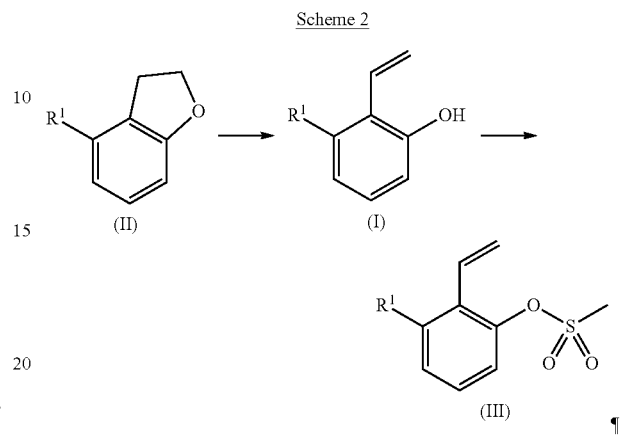

$R^1$ is Cl, Br or methyl

Examples

The present invention is elucidated in more detail by the examples which follow, without restricting the invention to these examples.

3-Chloro-2-vinylphenol (Ia)

Potassium hydroxide powder (85%, 22.6 g, 342.9 mmol) is added to a solution of 4-chloro-2,3-dihydro-1-benzofuran (IIa) (19.0 g, 114.3 mmol) in N,N-dimethylacetamide (75 ml) at 20° C., the mixture is heated to 120° C. and stirred at this temperature for 1 hour. The reaction mixture was cooled to ca. 10-15° C., diluted with water (150 ml) and brought to a pH of 1 by slow addition of 37% hydrochloric acid (40 ml). The aqueous phase was extracted twice with toluene (100 ml each time), the combined organic phases washed once with 10% hydrochloric acid (30 ml) and concentrated under reduced pressure to a residual volume of ca. 100 ml. The solution thus obtained is used directly in the next step. Analytical data for 3-chloro-2-vinylphenol are as follows: $^1$H-NMR (CDCl$_3$, 400 MHz) δ (ppm)=7.08 (dd, J=8.0, 8.0 Hz, 1H), 6.96 (d, J=8.0 Hz, 1H), 6.84 (d, J=8.0 Hz, 1H), 6.79 (dd, J=12.0 Hz, 12.0 Hz, 1H), 5.74 (d, J=12.0 Hz, 1H), 5.73 (s, 1H), 5.68 (d, J=12.0 Hz, 1H).

3-Bromo-2-vinylphenol (Ib)

$^1$H-NMR (DMSO-d6, 400 MHz) δ (ppm)=10.20 (s, 1H), 7.08 (dd, J=8.0, 1.3 Hz, 1H), 6.99 (t, J=8.0 Hz, 1H), 6.89 (dd, J=8.0, 1.0 Hz, 1H), 6.77 (dd, J=17.8, 12.1 Hz, 1H), 6.08 (dd, J=17.8, 2.5 Hz, 1H), 5.51 (dd, J=12.1, 2.5 Hz, 1H).

3-Methyl-2-vinylphenol (Ic)

$^1$H-NMR (DMSO-d6, 400 MHz) δ (ppm)=9.45 (s, 1H), 6.93 (t, J=7.8 Hz, 1H), 6.73 (dd, J=17.9, 11.8 Hz, 1H), 6.69 (d, J=7.8, 1.0 Hz, 1H), 6.63 (d, J=7.8 Hz, 1H), 5.76 (dd, J=17.9, 2.5 Hz, 1H), 5.41 (dd, J=11.9, 2.5 Hz, 1H), 2.27 (s, 3H).

3-Chloro-2-vinylphenyl Methanesulphonate (IIIa)

The toluene solution of Ia obtained in the step above was cooled to 0-5° C. and triethylamine (17.5 ml, 125.7 mmol) was added. A 50% solution of methanesulphonyl chloride (9.7 ml, 125.7 mmol) in toluene was metered in over a period of 1 hour at a temperature of 0-5° C. and, after addition was complete, the mixture was stirred at 20° C. for 30 min. Subsequently, the reaction mixture was brought to a pH of 1 by slow addition of 10% hydrochloric acid (50 ml) at 10-15° C. and the aqueous phase extracted twice with a mixture of toluene/tert-butyl methyl ether 4:1 (50 ml each time). The combined organic phases were concentrated under reduced pressure and the residue was recrystallized from ethanol (15 ml) (23.7 g, 89% of theory). $^1$H-NMR (CDCl$_3$, 400 MHz) δ (ppm)=7.36 (dd, J=8.0, 1.2 Hz, 1H), 7.34 (dd, J=8.0, 1.2 Hz, 1H), 7.23 (t, J=8.0 Hz, 1H), 6.76 (dd, J=18.0 Hz, 11.7 Hz, 1H), 5.91 (dd, J=18.0, 1.6 Hz, 1H), 5.73 (dd, J=11.8, 1.4 Hz, 1H), 3.11 (s, 3H).

3-Bromo-2-vinylphenyl Methanesulphonate (IIIb)

$^1$H-NMR (CDCl$_3$, 400 MHz) δ (ppm)=7.56 (dd, J=8.1, 1.1 Hz, 1H), 7.38 (dd, J=8.1, 1.1 Hz, 1H), 7.16 (t, J=8.1 Hz, 1H), 6.72 (dd, J=18.0 Hz, 11.8 Hz, 1H), 5.84 (dd, J=18.0, 1.4 Hz, 1H), 5.71 (dd, J=11.6, 1.4 Hz, 1H), 3.11 (s, 3H).

3-Methyl-2-vinylphenyl Methanesulphonate (IIIc)

$^1$H-NMR (CDCl$_3$, 400 MHz) δ (ppm)=7.23 (dd, J=7.8, 1.8 Hz, 1H), 7.18 (t, J=7.8 Hz, 1H), 7.14 (dd, J=7.5, 1.4 Hz, 1H), 6.71 (dd, J=17.8 Hz, 11.8 Hz, 1H), 5.65 (dd, J=11.8, 1.6 Hz, 1H), 5.63 (dd, J=17.8, 1.6 Hz, 1H), 3.09 (s, 3H), 2.37 (s, 3H).

The invention claimed is:

1. A method for preparing substituted styrene derivative of formula (I):

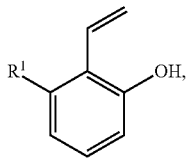
(I)

where
$R^1$ is Cl (Ia), Br (Ib) or methyl (Ic),
comprising reacting a dihydrobenzofuran derivative of formula (II)

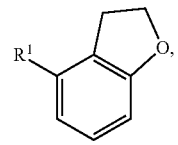
(II)

where
$R^1$ is Cl, Br or methyl,
by heating in the presence of an alkoxide or hydroxide base
to give a compound of formula (I).

2. The method according to claim 1, wherein the radical definitions of formulae (I) and (II) are as follows:
$R^1$ is Cl.

3. The method according to claim 1, wherein the base used is potassium tert-butoxide, sodium tert-butoxide, sodium methoxide, sodium ethoxide, potassium methoxide or potassium hydroxide.

4. The method according to claim 1, further comprising using one or more of an amide or ether solvent or mixtures of amide solvents with ethers or aromatic solvents as solvent.

5. The method according to claim 1, further comprising using one or more solvents comprising one or more of DMAc, DMF or diglyme or mixtures of DMAc or DMF with THF, 2-methyl-THF, dioxane, DME, toluene, xylene, chlorobenzene or 1,2-dichlorobenzene.

6. The method according to claim 1, wherein one of the following combinations of solvent and base is used for the reaction:
   a) diglyme in combination with potassium hydroxide
   b) DMAc in combination with potassium hydroxide
   c) DMF in combination with potassium hydroxide
   d) solvent mixture of DMAc with toluene, xylene, chlorobenzene, 1,2-dichlorobenzene, dioxane, DME, 2-methyl-THF or THF in combination with potassium hydroxide
   e) solvent mixture of DMF with toluene, xylene, chlorobenzene, 1,2-dichlorobenzene, dioxane, DME, 2-methyl-THF or THF in combination with potassium hydroxide
   f) DMAc, DMF, THF, 2-methyl-THF, dioxane, DME, anisole or diglyme or mixtures of these solvents in combination with potassium tert-butoxide
   g) potassium hydroxide as inorganic base and potassium tert-butoxide as organic base.

\* \* \* \* \*